United States Patent [19]

Grabley et al.

[11] Patent Number: 4,945,108
[45] Date of Patent: Jul. 31, 1990

[54] ANGUCYCLINONES FROM STREPTOMYCETES, A PROCESS FOR THE PREPARATION THEREOF, AND THE USE THEREOF

[75] Inventors: Susanne Grabley, Königstein/Taunus; Joachim Wink, Offenbach; Carlo Giani, Frankfurt; Gerhard Seibert, Darmstadt; Wolfgang Raether, Dreieich; Susanne Dobreff; Axel Zeeck, both of Göttingen, all of Fed. Rep. of Germany

[73] Assignee: Hoechst Aktiengesellschaft, Frankfurt am Main, Fed. Rep. of Germany

[21] Appl. No.: 342,061

[22] Filed: Apr. 24, 1989

[30] Foreign Application Priority Data

Apr. 26, 1988 [DE] Fed. Rep. of Germany ....... 3813967

[51] Int. Cl.$^5$ .................... C07D 303/17; C07D 69/00; C07D 49/543; A61K 31/335
[52] U.S. Cl. .................................. 514/475; 514/510; 514/680; 549/543; 560/139; 568/326
[58] Field of Search ................ 549/543; 514/475, 680; 560/6, 139; 568/326

[56] References Cited

PUBLICATIONS

Katsura et al., "Directed Ortho Mitalation Reactions" *Tetrahedron Letters* vol. 26, No. 1, pp. 9–12 (1985).

*Primary Examiner*—Richard L. Raymond
*Assistant Examiner*—Peter G. O'Sullivan
*Attorney, Agent, or Firm*—Finnegan, Henderson, Farabow, Garrett and Dunner

[57] ABSTRACT

New angucyclinones with a therapeutic action can be prepared with the aid of a strain of the genus Streptomyces.

3 Claims, No Drawings

ANGUCYCLINONES FROM STREPTOMYCETES, A PROCESS FOR THE PREPARATION THEREOF, AND THE USE THEREOF

DESCRIPTION

It is known that Streptomyces spec. synthesizes under conventional culture conditions an angucyclinone called ochromycinone [Bowie J. H., Johnson A. W. Tetrahedron Letters 16, 1449 (1967)].

It has now been found, surprisingly, that Streptomyces spec. DSM 4201 and DSM 4202 form, besides ochromycinone, new angucyclinones with an antimicrobial action and activity against protozoa.

Hence the invention relates to:
1. A compound of the general formula I

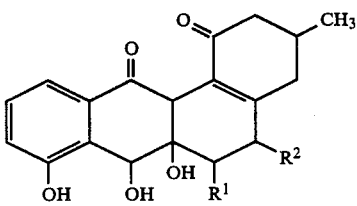

in which, independently of one another,
$R^1$ can be hydroxyl and
$R^2$ can be hydrogen, or
$R^1$ and $R^2$ represent, together with the carrying carbon atoms, an oxirane ring,
as well as the ($C_1$ to $C_5$)-acyloxy compounds derivatized on the hydroxyl groups indicated in formula I.

2. A process for the preparation of the compound of the general formula I, which comprises
(a) cultivating Streptomyces spec. DSM 4201 and DSM 4202 until the compound of the general formula I accumulates in the culture medium and
(b) where appropriate isolating and acylating the compound.

The invention is described in detail hereinafter, especially in its preferred embodiments. The invention is also defined in the patent claims.

The compound of the general formula I can be prepared with the aid of Streptomyces spec. DSM 4201 and DSM 4202. The strains were deposited in accordance with the conditions of the Budapest Treaty on Aug. 5, 1987, at the Deutsche Sammlung von Mikroorganismen (German Microorganism Collection) under the stated number.

Streptomyces spec. DSM 4201 and DSM 4202 have the following characteristic features:

| | |
|---|---|
| Spore color | gray |
| Spore chain | retinaculum apertum |
| Spore surface | smooth |
| Melanin formation | negative |
| Pigment formation | |
| substrate mycelium | Endo: negative |
| | Exo: negative |
| aerial mycelium | Endo: negative |
| | Exo: negative |
| Sugar and sugar alcohol utilization | arabinose, xylose, rhamnose, raffinose, mannitol, inositol, fructose, sucrose. |

In place of Streptomyces spec. DSM 4201 and DSM 4202 it is also possible to use the mutants and variants thereof as long as they are likewise able to produce the compound of the general formula I. Such mutants can be generated in a manner known per se by physical means, for example irradiation, such as with ultraviolet or X-rays, or chemical mutagens such as, for example, ethyl methanesulfonate (EMS), N-methyl-N'-nitro-N-nitrosoguanidine (MNNG) or 2-hydroxy-4-methoxybenzophenone (MOB).

Suitable and preferred carbon sources for the aerobic fermentation are assimilable carbohydrates and sugar alcohols such as glucose, lactose or D-mannitol, as well as carbohydrate-containing natural products such as malt extract. Suitable and preferred nitrogen-containing nutrients are: amino acids, peptides and proteins as well as the degradation products thereof, such as peptones or tryptones, also meat extracts, milled seeds, for example of corn, wheat, beans, soybean or the cotton plant, distillation residues from the production of alcohol, meat meals or yeast extracts, but also ammonium salts and nitrates. The nutrient solution can additionally contain, for example, chlorides, carbonates, sulfates or phosphates of the alkali metals or alkaline earth metals, iron, zinc and manganese as additional inorganic salts.

The formation of the compound of the general formula I takes place especially well in a nutrient solution which contains glycerol in concentrations of 0.5 to 6%, preferably 2 to 4%, and soybean meal in concentrations of 0.1 to 4%, preferably 0.5 to 2%, in each case based on the weight of the complete nutrient solution.

The fermentation is carried out aerobically, that is to say, for example, submerged with shaking or stirring in shaken flasks or fermenters, where appropriate introducing air or oxygen. The fermentation can be carried out in a temperature range from about 18° to 40° C. preferably at about 25° to 30° C., especially at 28° to 30° C. The microorganism is cultivated under the said conditions until the stationary phase is reached, for about 60 to 120 hours, preferably 70 to 75 hours.

The cultivation is advantageously carried out in several stages, i.e. one or more precultures are initially prepared in a liquid nutrient medium and are then transferred into the actual production medium, the main culture, for example in the ratio 1:10 by volume. The preculture is obtained, for example, by transferring a sporulated mycelium into a nutrient solution and leaving it to grow for about 48 to 72 hours. The sporulated mycelium can be obtained by leaving the strain to grow for about 7 days on a solid or liquid nutrient medium, for example yeast-malt agar.

The progress of the fermentation can be monitored by means of the pH of the culture or of the mycelium volume, by thin-layer chromatography or testing the biological activity.

The angucyclinones of the general formula I are present both in the mycelium and in the culture broth. It is therefore expedient for the isolation of the substance to work up both. It is advantageous before the actual working up to separate the mycelium from the culture broth, for example by filtration or centrifugation. The compound of the general formula I can then be isolated from the supernatant or filtrate, expediently in the pH range 2 to 8, preferably at pH values from 5 to 7. The substance can be extracted with conventional agents, for example polar solvents, for example lower alkanols. However, it is advantageous to pass the liquid over an adsorber resin such as, for example, those based on polystyrene. The elution can then be carried out with a polar solvent, preferably lower alkanols such as, for example, methanol, which are possibly also mixed with water. The solvent can be removed from the eluate by distillation, and the aqueous residue containing the angucyclinones can be dried.

The angucyclinones of the general formula I are colorless amorphous solids which are readily soluble in methanol, acetone, DMSO, dioxane and chloroform but not in water and alkanes. The desired acyloxy derivatives are obtained by base-catalyzed acylation of the hydroxyl groups with an appropriate anhydride. The compounds of the general formula I, as well as the ($C_1$ to $C_5$)-acyloxy derivatives, preferably ($C_1$ to $C_2$)-acyloxy derivatives, can be incorporated in pharmaceutical formulations appropriate for their stability. The antibacterial and antifungal action can be shown in vitro in the agar diffusion test. The angucyclinones additionally exhibit a potent action against protozoa, especially against *Trichomonas vaginalis*.

The invention is explained in more detail in the examples which follow. Percentage data relate, as in the previous description too, to weight. The Rf values stated below relate to SilG/UV 254+366; 0.25 mm layer thickness from Macherey & Nagel.

EXAMPLES 1.(a) Preparation of a suspension of spores of the producer strain:

100 ml of nutrient solution (4 g of yeast extract, 10 g of malt extract, 4 g of glucose, 1 l of tap water, pH before sterilization 7.3) in a 500 ml Erlenmeyer flask are inoculated with the strain DSM 4201 and DSM 4202 and incubated at 27° C. and 120 rpm on a rotating shaker for 72 hours. Subsequently 20 ml of culture liquid are uniformly distributed in a 500 ml Erlenmeyer flask containing the nutrient medium of the abovementioned composition to which 20 g of agar/l have been added for solidification, and are decanted. The cultures are incubated at 27° C. for 10 to 14 days. The spores which have resulted after this time in one flask are rinsed out with 500 ml of deionized water which contains one drop of a commercially available nonionic surfactant (Triton X100 from Serva), and immediately used further or stored at −22° C.

(b) Preparation of a culture or preculture of the producer strain in an Erlenmeyer flask A 500 ml Erlenmeyer flask containing 100 ml of a nutrient solution composed of 2% meat meal, 10% malt extract, 1% calcium carbonate and water ad 100% (pH 7.2 before autoclaving) is inoculated with a culture grown in a slant tube or with 0.2 ml of spore suspension and incubated at 27° C. and 120 rpm in a shaker. The maximum antibiotic production is reached after 72 hours. A 48-hour old submerged culture (5%) from the same nutrient solution suffices to inoculate 10 and 100 l fermenters.

2. Preparation of the angucyclinones

A 10 l fermenter is operated under the following conditions:

| Nutrient medium | 30 g/l glycerol |
| | 2 g/l casein peptone |
| | 1 g/l $K_2HPO_4$ |
| | 1 g/l NaCl |
| | 0.5 g/l $MgSO_4 \cdot 7H_2O$ |
| | 5 ml/l trace element solution |
| Trace elements | 3 g/l $CaCl_2 \cdot 2H_2O$ |
| | 1 g/l $FeC_6O_7H_5$ |
| | 0.2 g/l $MnSO_4$ |
| | 0.1 g/l $ZnCl_2$ |
| | 0.025 g/l $CuSo_4 \cdot 5H_2O$ |
| | 0.02 g/l $Na_2B_4O_7 \cdot 10H_2O$ |
| | 0.004 g/l $CoCl_2$ |
| | 0.01 g/l $Na_2MoO_4 \cdot 2H_2O$ |
| Incubation time | 72 hours |
| Incubation temperature | 30° C. |
| Stirrer speed | 250 rpm |
| Aeration | 4 l of air/min. |

Foam formation can be suppressed by repeated addition of a few drops of ethanolic polyol solution. The production maximum is reached after about 70 hours (pH=5.3).

3. Isolation of the angucyclinones

After the fermentation of DSM 4201 and DSM 4202, the culture broth is filtered with the addition of 2% Celite as filtration aid. The mycelium is extracted with acetone, the organic phase is evaporated, and the aqueous residue is added to the culture filtrate. The culture filtrate is passed through an adsorber resin based on polystyrene (XAD2, from Fluka). The effluent is discarded, and the angucyclinones are eluted with methanol/$H_2O$ (80:20). The eluate is distilled. The angucyclinones are present in the distillation residue.

4. Isolation and characterization of the compounds

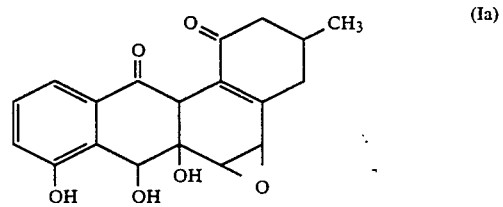

The compounds Ia and Ib are obtained from the culture filtrate from Streptomyces DSM 4201 and DSM 4202.

The lyophilisate from a 100 l fermentation was suspended with 10 g of silica gel in a little mobile phase and loaded onto a prepared silica gel column (10×25 cm; silica gel 0.04–0.063 mm) and separated into 2 fractions with chloroform/methanol (2 l, 20:1; 5 l l gradient to 9:1) under medium pressure:

Fraction 1: 20 g of Ib, Rf=0.37 (chloroform/methanol 9:1, v/v) with a little Ia, Rf=0.72 (chloroform/methanol=9:1), Fraction 2: 11 g of Ib, Rf=0.37 (chloroform/methanol=9:1, v:v).

The fermentation provided 20 mg/l Ia and 111 mg/l Ib.

Compound Ib

Melting point 95° C.

Rf=0.37 (chloroform/methanol=9:1, v:v).

IR (KBr): ν=3420, 2960, 1680, 1640, 1595, 1470, 1390, 1295, 1078 $cm^{-1}$.

UV (MeOH): λ (lg ε)=257 (3.8), 326 (3.2), 353 (3.2) nm $^1$H NMR (200 MHz; DMSO-d$_6$, 37° C.): δ=9.85–9.2 (s; 1H), 7.0–6.8 (m; 3H), 5.05 (s; 1H), 5.00–4.65 (s; 1H, H/D), 4.50–4.24 (s; 1H, H/D), 3.91 (s; 1H), 3.01 (dd, J=8.0 Hz; J=8.0 Hz; 1H), 2.20–1.70 (m; 7H), 0.76 (d, J=5.0 Hz; 3H) ppm.

$^{13}$C NMR (200 MHz, CDCl$_3$): δ=199.8 (C=O), 195.9 (C=O), 157.2 (C), 155.5 (C), 130.9 (C), 129.9 (CH), 128.2 (C), 126.3 (C), 121.8 (CH), 118.7 (CH), 74.5 (C), 66.6 (CH), 63.2 (CH), 47.6 (CH), 45.3 (CH$_2$), 38.9 (CH$_2$), 38.3 (CH$_2$), 29.1 (CH), 20.9 (CH$_3$) ppm.

Fast atom bombardment MS: (positive ions) m/e=345 (MH$^+$, 100%). (negative ions) m/e=343 (M-H$^-$, 100%)

EI-MS (70 eV): m/e=306 (m-2H$_2$O-2H, 49%; high resolution: 306.0893, corresponding to C$_{19}$H$_{14}$O$_4$).

Molecular formula: C$_{19}$H$_{20}$O$_6$ (344.3676 g mol$^{-1}$).

Two fractions were obtained by a second column chromatography of the 1st fraction, which was carried out exactly as the separation described above:

Fraction 1: 5.46 g, Ia Rf=0.72 (chloroform/methanol=9:1),

Fraction 3: 458 mg Ib, Rf=0.37 (chloroform/methanol=9:1).

Compound Ia

Melting point: 257° C.

Rf=0.72 (chloroform/methanol=9:1, v:v).

[α]$_D^{20}$ +28.5° (c=1.05 CH$_3$OH).

IR (KBr): υ=3500–3200, 2960, 2930, 2900, 2870, 1690 (sh), 1675, 1650, 1623, 1580, 1455, 1312, 1300 cm$^{-1}$.

UV (CHCl$_3$:CH$_3$OH=1:1): λ (lg ε)=258 (3.9), 314 (3.4).

$^1$H NMR (200 MHz; DMSO-d$_6$, 37° C.): δ=7.3–7.2 (m; 2H), 7.1–7.0 (m; 1H), 5.25–5.1 (m; 1H, H/D), 5.03 (s, 1H), 3.63 (d, J=1.5 Hz; 1H), 3.45 (d, J =4.0 Hz), 3.37 (d, J=4.0 Hz; 1H), 3.4–3.2 (m; 1H, H/D), 2.7–2.0 (m; 5H), 0.99 (d, J=6.0 Hz; 3H) ppm.

$^1$H NMR (200 MHz, CDCl$_3$/CD$_3$OD): δ=7.50 (dd, J=1.2 Hz, J=8.0 Hz; 1H), 7.30 (dd, J=8.0 Hz, J=8.0 Hz; 1H), 7.08 (dd, J=1.2 Hz, J=8.0 Hz; 1H), 5.18 (s; 1H), 3.85 (dd, J=1.5 Hz, J=3.0 Hz; 1H), 3.67 (d, J=4.0 Hz; 1H), 3.44 (d, J=4.0 Hz; 1H), 2.27–2.04 (m; 5H), 1.09 (d, J=6 Hz; 3H) ppm.

$^{13}$C NMR (200 MHz, acetone-d$_6$/CD$_3$OD): δ=198.4 (C=O), 197.7 (C=O), 157.5 (C), 153.8 (C), 134.7 (C), 132.7 (C), 130.1 (CH), 127.0 (C), 121.2 (CH), 119.1 (CH), 75.6 (C), 68.8 (CH), 58.6 (CH), 54.1 (CH), 49.9 (CH), 38.4 (CH$_2$), 31.0 (CH$_2$), 30.5 (CH), 21.2 (CH$_3$) ppm.

Fast atom bombardment MS (negative ions): m/e=341 (m-H$_2$O-H).

Molecular formula C$_{19}$H$_{29}$O$_7$ (360.3670).

5. Preparation and characterization of the acetyl derivatives of compound Ib

Tri-O-acetyl-Ib:

313 mg (0.91 mmol) of Ib were stirred in 20 ml of pyridine/acetic anhydride (=1:1) at room temperature for one day. The reaction mixture was poured into 50 ml of ice-water and, after 30 min, the aqueous phase was extracted three times with 50 ml of diethyl ether each time. The combined extracts were extracted by shaking with 50 ml of 2M HCl, the latter were dried over sodium sulfate, and the solvent was evaporated off in vacuo.

The column chromatography was carried out as in the previous example. It provided one main product: 221.7 mg of tri-O-acetyl-Ib (52%).

Melting point: 95°–98° C.

Rf=0.98 (chloroform/methanol=9:1, v:v).

IR (KBr): υ=3440, 2950, 1760, 1735, 1690, 1650, 1600, 1425, 1365, 1230, 1188, 1040, 1020 cm$^{-1}$.

UV (MeOH): λ (lg ε)=253 (3.7), 290 (3.2) nm.

$^1$H NMR (200 MHz; CDCl$_3$): δ=7.90 (dd, J=1.2 Hz, J=7.8 Hz; 1H), 7.53 (dd, J=7.8 Hz, J=8.0 Hz; 1H), 7.32 (dd, J=1.2 Hz, J=8.0 Hz; 1H), 6.55 (s; 1H), 4.75 (dd, J=7.8 Hz, J=9.0 Hz; 1H), 4.53 (s; 1H), 3.60 (s; 1H, H/D), 2.8–1.95 (m; 7H), 2.41 (s; 3H), 2.08 (s; 3H), 2.14 (s; 3H), 1.08 (d, J=5.5 Hz; 3H) ppm.

—C NMR (200 MHz; CDCl$_3$): δ197.9 (C=O), 193.2 (C=O), 171.2 (C=O), 169.9 (C=O), 169.4 (C=O), 154.4 (C), 149.5 (C), 132.2 (C), 130.9 (CH), 128.8 (C), 128.8 (CH), 127.7 (C), 125.6 (CH), 72.98 (C), 69.3 (CH), 64.5 (CH), 47.6 (CH), 45.2 (CH$_2$), 38.6 (CH$_2$), 34.7 (CH$_2$), 29.0 (CH), 20.8 (2CH$_3$), 20.7 (2CH$_3$), ppm.

EI-MS (70 eV): m/e=470 (M$^+$, 1%), 368 (M-2Ac-H$_2$O+2H, 1%).

Molecular formula: C$_{22}$H$_{26}$O$_9$ (470.3543 g mol$^{-1}$).

Di-O-acetyl-Ib:

800 mg (2.32 mmol) of Ib were stirred in 10 ml of acetic anhydride/glacial acetic acid (=1:1) at room temperature for 2 days. The reaction mixture was poured into 100 ml of ice-water and, after 2 h, extracted three times with 20 ml of chloroform each time. The combined organic phases were extracted twice with 20 ml of dilute sodium bicarbonate each time and then with 20 ml of water each time, dried over sodium sulfate and evaporated. The crude product was fractionated by column chromatography as described above: 463.7 mg of di-O-acetyl-Ib (47%).

Melting point: +100° C.

Rf=0.81 (chloroform/methanol=9:1, v:v).

IR (KBr): υ=3440, 2945, 2929, 1760, 1735, 1680, 1650, 1600, 1368, 1230, 1190 cm$^{-1}$.

UV (CH$_3$OH): λ (lg ε)=220 (3.9),˙ 246 (4.00), 2.90 (3.1) nm.

$^1$H NMR (200 MHz; CDCl$_3$): δ=7.62 (dd, J=1.2 Hz, J=7.8 Hz; 1H), 7.53 (dd, J=7.8 Hz, J=8.0 Hz; 1H), 7.34 (dd, J=1.2 Hz, J=8.0 Hz; 1H), 6.57 (s; 1H), 4.50 (s; 1H), 3.72 (ddd, J=7.0 Hz, J≈8 Hz, J≈8 Hz; 1H) 3.08 (s; 1H, H/D), 2.8–2.5 (s; 1H, H/D), 2.8–2.0 (m; 7H), 2.41 (s; 3H), 2.08 (s; 3H), 1.06 (d, J=6.0 Hz; 3H) ppm.

$^{13}$C NMR (200 MHz; CDCl$_3$): δ197.8 (C=O), 193.9 (C=O), 171.1 (C=O), 171.0 (C=O), 154.8 (C), 149.2 (C), 132.2 (C), 130.99 (CH), 129.2 (C), 128.3 (CH), 127.8 (C), 125.8 (CH), 74.4 (C), 66.7 (CH), 65.1 (CH), 47.2 (CH), 45.3 (CH$_2$), 38.8 (CH$_2$), 37.5 (CH$_2$), 29.1 (CH), 20.9 (2CH$_3$), 20.9 (CH$_3$), 20.8 (CH$_3$ ) ppm.

EI-MS (70 eV): m/e=428 (M$^+$, 1%), 368 (M-Ac-H$_2$O+H, 22%), 308 (M-2Ac-2H$_2$O+2H, 70%).

Molecular formula: C$_{23}$H$_{24}$O$_8$ (428.4509 g mol$^{-1}$).

O-Acetyl-O-methyl-Ib:

390 mg (0.83 mmol) of tri-O-acetyl-Ib were dissolved in 10 ml of CHCl$_3$ and stirred with 15 drops of 1M methanolic sodium hydroxide for 12 h. The pH was adjusted to 6.5 with 0.1M hydrochloric acid, and the reaction mixture was extracted three times with 50 ml of water each time. 100 ml of toluene were added to the organic phase which was then evaporated in vacuo and chromatographed as described above: 165 mg of O-acetyl-O-methyl-Ib (48%).

Melting point: 105° C.

Rf=0.83 (chloroform/methanol=9:1, v:v).

IR (KBr): ν=3440, 2950, 2830, 1735, 1680, 1660, 1590, 1469, 1372, 1288, 1245 cm$^{-1}$.

UV (MeOH): λ (lg ε)=228 (4.0), 252 (3.9), 323 (3.3) nm.

$^1$H NMR (200 MHz; CDCl$_3$): δ=7.58 (dd, J=1 Hz, J=8 Hz; 1H), 7.30 (bs; 1H, H/D), 7.22 (dd, J=8 Hz, J=8 Hz; 1H), 6.87 (dd, J=1 Hz; J=8 Hz; 1H), 5.00 (s; 1H), 4.84 (dd, J=7 Hz, J=8.7 Hz; 1H), 4.49 (s; 1H), 3.46 (s; 1H, H/D), 2.8–2.0 (m; 7H), 2.13 (s; 3H), 1.09 (d, J=6 Hz; 3H) ppm.

$^{13}$C NMR (200 MHz; CDCl$_3$): δ=199.0 (C=O), 195.1 (C=O), 170.8 (C=O), 155.9 (C), 154.9 (C), 131.5 (C), 130.2 (CH), 128.7 (C), 123.9 (C), 121.4 (CH), 119.6 (CH), 74.4 (C), 71.4 (CH), 68.7 (CH), 57.4 (OMe), 48.98 (CH), 45.2 (CH$_2$), 38.8 (CH$_2$X), 28.97 (CH), 20.7 (CH$_3$) ppm.

EI-MS (70 eV): m/e=400 (M+, 3%).

Molecular formula: C$_{22}$H$_{24}$O$_7$ (400.4401 gmol$^{-1}$).

Anthrone derivative from Ib:

200 mg (0.58 mmol) of Ib, 261 mg (1.74 mmol) of sodium iodide and 199 mg (1.12 mmol) of p-toluenesulfonic acid in 10 ml of dry acetonitrile were stirred at room temperature for 5 days. The reaction mixture was poured into 50 ml of ice-water and, after 30 min, the mixture was extracted three times with 30 ml of methylene chloride each time, and the combined organic phases were extracted twice with 50 ml of aqueous sodium thiosulfate solution each time.

The organic phase was dried over sodium sulfate and then evaporated in vacuo. Column chromatography on silica gel (0.063 mm, column: 2.5 cm×30 cm) with n-hexane/ethyl acetate 95:5 (3 l) via a gradient to n-hexane/ethyl acetate 80:20 (4 l) under a pressure of 1 bar yielded 20.2 mg of anthrone derivative (11%), Melting point: 203°–219° C.

Rf=0.84 (n-hexane/ethyl acetate 4:1, v:v).

IR (KBr): ν=3450, 2945, 2920, 2860, 1620, 1610, 1585 cm$^{-1}$.

UV (CHCl$_3$:MeOH 1:1, V:V): λ (lg ε)=358 (3.2), 286 (3.7), 248 (3.9) nm.

$^1$H NMR (200 MHz; CDCl$_3$): δ=12.79 (s; 1, H/D), 8.57 (d, J=8.0 Hz; 1H), 7.50 (dd, J=8.0 Hz, J=8.0 Hz; 1H), 7.39 (d, J=8.0 Hz; 1H), 7.03 (dd, J=1.0 Hz, J=8.0 Hz; 1H), 6.88 (dd, J=0.8 Hz, J=8.0 Hz; 1H), 4.84 (s; 2H), 3.2–2.3 (m; 5H), 1.17 (d, J=6.0 Hz; 3H) ppm.

$^{13}$C NMR (200 MHz; CDCl$_3$): δ199.9 (C=O), 188.6 (C=O), 162.6 (C), 151.3 (C), 143.4 (C), 143.0 (C), 135.96 (CH), 131.6 (CH), 130.6 (C), 129.3 (C), 128.3 (CH), 119.1 (CH), 115.7 (C), 114.5 (CH), 49.2 (CH$_2$), 39.8 (CH$_2$), 32.9 (CH$_2$), 29.7 (CH), 21.1 (CH$_3$) ppm.

EI-MS (70 eV): m/e=292 (M, 100%; High resolution=292.1099 corresponding to C$_{19}$H$_{16}$O$_3$).

Molecular formula: C$_{19}$H$_{16}$O$_3$ (292.3442 g mol$^{-1}$).

We claim:

1. A compound of the general formula I

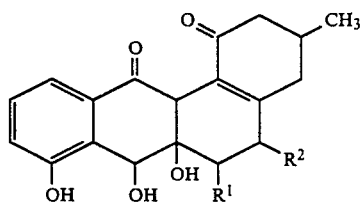

in which, independently of one another,

R$^1$ can be hydroxyl and

R$^2$ can be hydrogen, or

R$^1$ and R$^2$ represent, together with the carrying carbon atoms, an oxirane ring, as well as the (C$_1$toC$_5$)-acyloxy compounds derivatized on the hydroxyl groups indicated in formula I.

2. A method of treating a human being or an animal for an infectious disease caused by bacteria, fungi, or protozoa, which comprises:

administering to said human being or animal an amount of the compound of formula I as claimed in claim 1 effective to treat said infectious disease.

3. A pharmaceutical composition which comprises:

one or more pharmaceutically acceptable excipients, and an effective amount of a compound of formula I as claimed in claim 1.

* * * * *